United States Patent
Henry et al.

(10) Patent No.: US 11,312,976 B2
(45) Date of Patent: Apr. 26, 2022

(54) METHODS FOR RECOVERING WATER-IMMISCIBLE ISOPRENOID COMPOUNDS FROM MICROBIAL BIOMASS

(71) Applicant: AMYRIS, INC., Emeryville, CA (US)

(72) Inventors: Ronald Ray Henry, Emeryville, CA (US); Joshua Steven Leng, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

(21) Appl. No.: 17/255,031

(22) PCT Filed: Jun. 27, 2019

(86) PCT No.: PCT/US2019/039536
§ 371 (c)(1),
(2) Date: Dec. 22, 2020

(87) PCT Pub. No.: WO2020/006251
PCT Pub. Date: Jan. 2, 2020

(65) Prior Publication Data
US 2021/0230641 A1  Jul. 29, 2021

Related U.S. Application Data

(60) Provisional application No. 62/692,536, filed on Jun. 29, 2018.

(51) Int. Cl.
*C12P 5/02* (2006.01)
*C12N 1/18* (2006.01)
*C12R 1/865* (2006.01)

(52) U.S. Cl.
CPC ............... *C12P 5/02* (2013.01); *C12N 1/185* (2021.05); *C12R 2001/865* (2021.05)

(58) Field of Classification Search
CPC . C12P 5/02; C12P 5/007; C12N 1/185; C12R 2001/865
See application file for complete search history.

(56) References Cited

FOREIGN PATENT DOCUMENTS

| WO | WO 2010/115074 A1 | 10/2010 |
| WO | WO 2012/024186 A1 | 2/2012 |
| WO | WO 2019/030073 A1 | 2/2019 |

OTHER PUBLICATIONS

International search report and written opinion of PCT/US2019/039536 dated Sep. 24, 2019; 11 pages.
A. Heeres et al., "Microbial advanced biofuels production: overcoming emulsification challenges for large-scale operation", Trends In Biotechnology, vol. 32, No. 4, 2014, pp. 221-229.

*Primary Examiner* — Paul J Holland
(74) *Attorney, Agent, or Firm* — Squire Patton Boggs (US) LLP

(57) ABSTRACT

A method for recovering one or more water immiscible compounds comprising acidifying and disrupting the microbial biomass; heating the acidified, disrupted microbial biomass to form a heated, acidified disrupted microbial biomass; and contacting the heated, acidified, disrupted microbial biomass with a disulfonated surfactant in an amount sufficient to release at least 30% of the one or more water immiscible compounds from the microbial biomass.

29 Claims, 5 Drawing Sheets

METHODS FOR RECOVERING WATER-IMMISCIBLE ISOPRENOID COMPOUNDS FROM MICROBIAL BIOMASS

FIELD

Provided herein are compounds, compositions, and methods for recovering water-immiscible compounds from microbial biomass. The compounds, compositions, and methods are useful for production of water-immiscible compounds at large scale and high efficiency.

BACKGROUND OF THE INVENTION

The advent of synthetic biology has brought about the promise of fermentative microbial production of biofuels, chemicals, and biomaterials from renewable sources at industrial scale and quality. For example, functional non-native biological pathways have been successfully constructed in microbial hosts for the production of precursors to the antimalarial drug artemisinin (see, e.g., Martin et al., Nat Biotechnol 21:796-802 (2003)); fatty acid derived fuels and chemicals (e.g., fatty esters, fatty alcohols and waxes; see, e.g., Steen et al., Nature 463:559-562 (2010)); polyketide synthases that make cholesterol lowering drugs (see, e.g., Ma et al., Science 326:589-592 (2009)); or polyketides (see, e.g., Kodumal, Proc Natl Acad Sci USA 101:15573-15578 (2004)). However, the commercial success of synthetic biology will depend largely on whether the production cost of renewable products can be made to compete with, or out-compete, the production costs of their respective non-renewable counterparts.

In the fermentation production of compounds such as water-immiscible compounds, the hydrocarbon lipid molecule phase emulsifies with the aqueous phase to form a stabile emulsion which must be destabilized in order to recover the crude water-immiscible compound and separate it from the aqueous fractions of the broth. In microbial production of the water-immiscible compound farnesene, a sesqueterpene, two distinct types of emulsion have been observed: a light water-in-oil type emulsion which is readily destabilized with surfactants, and a more dense solids-stabilized emulsion, termed the "Dead Cell Layer" herein. This solids-stabilized emulsion is characterized by the presence of whole-cell and cell-debris associated water-immiscible compound. Typical emulsion breaking techniques such as surfactant addition, heat, and pH adjustment have been ineffective in breaking the dense emulsion layer. This has resulted in significant losses of product to the waste stream where the dense emulsion partitions during centrifugation and separation of the water-immiscible compound fraction from the aqueous fraction. There is a need for compositions and methods capable of recovering water-immiscible compounds from dead cell layers of fermentation media.

SUMMARY

Provided herein are compositions and methods for recovering one or more water-immiscible compounds from a microbial biomass. The methods generally comprise the steps of treating the microbial biomass by acidifying it and disrupting it. The acidifying and disrupting can be in any order. In certain embodiments, the acidifying precedes disrupting. In certain embodiments, the disrupting precedes acidifying. In certain embodiments, acidifying and disrupting are at the same time or overlap in time. Techniques for acidifying and disrupting are described herein. The resulting acidified, disrupted microbial biomass is then heated according to techniques described herein. Then, the resulting heated, acidified, disrupted microbial biomass is contacted with a surfactant capable of releasing an amount of the one or more water-immiscible compounds from the microbial biomass. Useful surfactants are described in detail herein. The one or more water-immiscible compounds is then recovered from the surfactant composition.

The methods and compositions are useful for the production of water-immiscible compounds by fermentation. Particular water-immiscible compounds for the methods and compositions include isoprenoids, polyketides, and fatty acids.

DETAILED DESCRIPTION OF THE PREFERRED EMBODIMENTS

Definitions

Figure 1A:
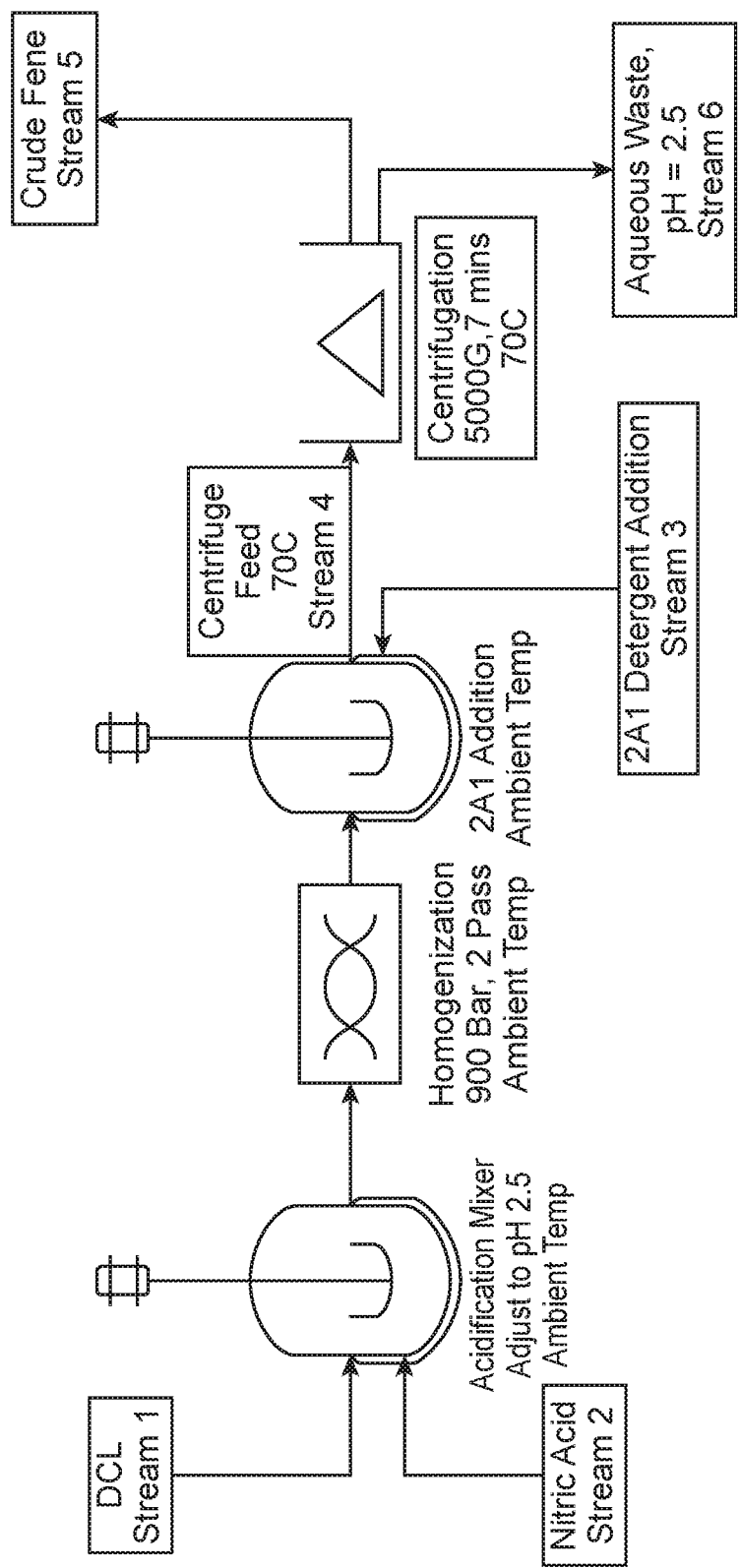
FIG. 1A provides a schematic of an exemplary system for carrying out certain methods provided herein.

When referring to the compositions and methods provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl", as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is selected from the group consisting of methyl, ethyl, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. In particular embodiments, the alkyl group is unsubstituted.

The term "substantially free of" or "substantially in the absence of" with respect to a composition refers to a composition that includes at least 85 or 90% by weight, in certain embodiments 95%, 98%, 99% or 100% by weight, of the designated enantiomer of that compound. In certain embodiments, in the methods and compounds provided herein, the compounds are substantially free of enantiomers.

Similarly, the term "isolated" with respect to a composition refers to a composition that includes at least 85, 90%, 95%, 98%, 99% to 100% by weight, of the compound, the remainder comprising other chemical species or enantiomers.

The term "host cell", as used herein, refers to any unicellular or multicellular organism. In certain embodiments, the host cell is suited for growth by fermentation. In certain embodiments, host cell produces one or more water-immiscible compounds. In certain embodiments, the host cell is recombinant, comprising one or more heterologous enzymes capable of producing one or more water-immiscible compounds. In certain embodiments, the host cell is recombinant, comprising one or more heterologous enzymes capable of producing one water-immiscible compound.

As used herein, the term "water-immiscible compound" refers to a compound of interest that does not form a solution when mixed with water. The water-immiscible compound may form a second layer with water, or an emulsion with water, or a combination thereof. In particular embodiments, the water-immiscible compound is a water-immiscible compound produced by a host cell.

As used herein, the term "native" or "endogenous" refers to a substance or process that can occur naturally in a host cell.

As used herein, the term "genetically modified" denotes a host cell that comprises a heterologous nucleotide sequence.

As used herein, the term "heterologous" refers to what is not normally found in nature. For example, the term "heterologous" when used with respect to a nucleic acid (DNA or RNA) or protein refers to a nucleic acid or protein that does not occur naturally as part of the organism, cell, genome, or DNA or RNA sequence in which it is present, or that is found in a cell or location or locations in the genome or DNA or RNA sequence that differ from that in which it is found in nature. The term "heterologous" when used with respect to a nucleic acid (DNA) can also refer to a nucleic acid which is operably linked to a promoter other than an endogenous promoter. The term "heterologous compound" refers to the production of a compound by a cell that does not normally produce the compound, or to the production of a compound at a level at which it is not normally produced by the cell.

As used herein, the phrase "heterologous enzyme" refers to an enzyme that is not normally found in a given cell in nature. The term encompasses an enzyme that is:
(a) exogenous to a given cell (i.e., encoded by a nucleotide sequence that is not naturally present in the host cell or not naturally present in a given context in the host cell); and
(b) naturally found in the host cell (e.g., the enzyme is encoded by a nucleotide sequence that is endogenous to the cell) but that is produced in an unnatural amount (e.g., greater or lesser than that naturally found) in the host cell.

As used herein, the term "naturally occurring" refers to what is found in nature. Conversely, as used herein, the term "naturally not occurring" refers to what is not found in nature but created by human intervention.

The terms "amino acid sequence," "peptide," "oligopeptide," "polypeptide" and "protein" are used here interchangeably, and refer to a polymeric form of amino acids of any length which may or may not be chemically or biochemically modified.

The terms "polynucleotide" and "nucleic acid" are used here interchangeably, referring to polymeric forms of any length, both ribonucleotides and deoxyribonucleotide.

The term "isolated nucleic acid," when applied to DNA, refers to a DNA molecule that is separated from sequences with which it is immediately contiguous in the naturally occurring genome of the organism in which it originated. An "isolated nucleic acid" also includes non-genomic nucleic acids such as cDNA or other non-naturally occurring nucleic acid molecules.

The term "cDNA" is defined herein as a DNA molecule which can be prepared by reverse transcription from a mature, spliced, mRNA molecule obtained from a cell. cDNA lacks intron sequences that are usually present in the corresponding genomic DNA.

As used herein, the phrase "operably linked" refers to a functional linkage between nucleic acid sequences such that the linked promoter and/or regulatory region functionally control expression of the coding sequence.

As used herein, the term "production" generally refers to an amount of water-immiscible compound produced by a genetically modified host cell provided herein. In some embodiments, production is expressed as a yield of the water-immiscible compound by the host cell. In other embodiments, production is expressed as a productivity of the host cell in producing the water-immiscible compound.

The term "yield" refers to production of a water-immiscible compound by a host cell, expressed as the amount of water-immiscible compound produced per amount of carbon source consumed by the host cell, by weight. In some embodiments, the term "yield" refers to the amount of water-immiscible compound produced per amount of total reducing sugar added to a fermenter vessel or a flask (i.e., grams of non-catabolic produced divided by grams of total reducing sugar added, expressed as percentage). The total reducing sugar is a unit of measurement of sugar in grams. A reducing sugar is any sugar that is capable of acting as a reducing agent because it has a free aldehyde group or a free ketone group. All monosaccharides, such as galactose, glucose, and fructose, are reducing sugars. For example, if 10 grams of water-immiscible compound is produced by feeding host cells 100 grams of glucose (i.e., 100 grams of reducing sugar), then the yield of product per reducing sugar is 10%.

As used herein, the term "productivity" refers to production of a water-immiscible compound by a host cell, expressed as the amount of water-immiscible compound produced (by weight) per amount of fermentation broth in which the host cell is cultured (by volume) over time (per hour).

The term "fermentation" is used to refer to culturing host cells that utilize carbon sources, such as sugar, as an energy source to produce a desired product.

The term "culture medium" refers to a medium which allows growth of cellular biomass and production of metabolites from host cells. It contains a source of carbon and may further contain a source of nitrogen, a source of phosphorus, a source of vitamins, a source of minerals, and the like.

As used herein, the term "fermentation medium" may be used synonymously with "culture medium." Generally, the term "fermentation medium" may be used to refer to a medium which is suitable for culturing host cells for a prolonged time period to produce a desired compound.

The term "medium" refers to a culture medium and/or fermentation medium. The "medium" can be liquid or semi-solid. A given medium may be both a culture medium and a fermentation medium.

The term "whole cell broth" refers to the entire contents of a vessel (e.g., a flask, plate, fermenter and the like), including cells, aqueous phase, compounds produced in hydrocarbon phase and/or emulsion. Thus, the whole cell broth includes the mixture of a culture medium comprising water, carbon source (e.g., sugar), minerals, vitamins, other dissolved or suspended materials, microorganisms, metabolites and compounds produced by host cells, and all other constituents of the material held in the vessel in which a water-immiscible compound is being made by the host cells.

The term "fermentation composition" is used interchangeably with "whole cell broth." The fermentation composition can also include an overlay if it is added to the vessel during fermentation.

The term "biosynthetic pathway" refers to a pathway with a set of anabolic or catabolic biochemical reactions for transmuting one chemical species into another, leading to the biosynthesis of a molecule. Gene products belong to the same "biosynthetic pathway" if they, in parallel or in series, act on the same substrate, produce the same product, or act on or produce a metabolic intermediate (e.g., metabolite) between the same substrate and metabolite end product.

As used herein, the term "promoter" refers to a synthetic or naturally-derived nucleic acid that is capable of conferring, activating or enhancing expression of a DNA coding sequence. A promoter may comprise one or more specific transcriptional regulatory sequences to further enhance expression and/or to alter the spatial expression and/or temporal expression of the coding sequence. A promoter may be positioned 5' (upstream) of the coding sequence under its control. The distance between the promoter and a coding sequence to be expressed may be approximately the same as the distance between that promoter and the native nucleic acid sequence it controls. As is known in the art, variation in this distance may be accommodated without loss of promoter function.

The phrase "strain stability" generally refers to the stability of heterologous compound production over extended periods of fermentation by a genetically modified host cell described herein. In particular, stability refers the ability of a microbe to maintain favorable production characteristics (i.e., high yield (grams of compound per gram of substrate) and/or productivity (grams per liter of fermentation broth per hour)) of a non-catabolic fermentation product over extended cultivation times, e.g., about 3 to 20 days. Genetic stability, which is the propensity of the producing microbial population to have little to no alteration of the intended allelic frequency of genes relevant to the production of product over time, plays a major role in the sustained output of product.

Unless indicated otherwise, the concentration unit of a water-immiscible compound or other component in a culture medium or solution is weight/volume percent. It is defined as concentration solute (w/v %)=(weight of solute (g)/volume of solution (mL))×100.

The term "transcriptional regulator" refers to a protein that control gene expression.

The term "transcriptional activator" refers to a transcriptional regulator that activates or positively regulates expression of a gene.

The term "transcriptional repressor" refers to a transcriptional regulator that represses or negatively regulates expression of a gene.

The term "cell-growth-affecting gene" or "nucleic acid encoding a cell-growth-affecting protein" refers to a nucleic acid that encodes a protein which affects cell growth (e.g., growth rate or cellular biomass) of a cell.

The term "essential gene" refers to a gene which is absolutely required to maintain life under optimum conditions where all nutrients are available.

The term "conditional essential gene" refers to a gene that is essential only under certain circumstances or growth conditions.

The term "regulon" refers to a group of genes or nucleic acids that are regulated by the same regulatory proteins (e.g., transcriptional regulators). The genes of a regulon have regulatory binding sites or promoters that are regulated by common transcriptional regulators. The group of genes or nucleic acids comprising a regulon can be located contiguously or non-contiguously in a genome of a host cell.

The term "inducible promoter" refers to a promoter that is activated by an inducer to induce the transcription of the gene(s) it controls.

The phrase "constitutive promoter" refers to a promoter that does not require the presence of an inducer to induce the transcription of the gene(s) it controls.

The term "expression," unless otherwise indicated, refers to the production of mRNA by transcription of the relevant gene and/or, to production of protein via gene transcription and then mRNA translation.

The term "catabolic" as used herein refers to the process of molecule breakdown or degradation of large molecules into smaller molecules.

The term "non-catabolic" refers to the process of constructing molecules from smaller units, and these reactions typically require energy. The term "water-immiscible compound" refers to a compound produced by a non-catabolic process.

The term "a," "an," and "the" means "at least one" unless the context clearly indicates otherwise.

Methods and Compositions

Provided herein are compositions and methods for recovering one or more water-immiscible compounds from a microbial biomass. In certain embodiments, the methods comprise the steps of acidifying the microbial biomass, disrupting the resulting composition, heating the resulting composition, contacting the resulting composition with a surfactant capable of releasing the one or more water-immiscible compounds from the microbial biomass, and recovering the one or more water-immiscible compounds.

Provided herein are compositions and methods for recovering one or more water-immiscible compounds from a microbial biomass. In certain embodiments, the methods comprise the steps of disrupting the microbial biomass, acidifying the resulting composition, heating the resulting composition, contacting the resulting composition with a surfactant capable of releasing the one or more water-immiscible compounds from the microbial biomass, and recovering the one or more water-immiscible compounds.

In certain embodiments, the microbial biomass is de-emulsified with a de-emulsifying surfactant deemed suitable by the person of skill. In some embodiments, the de-emulsifying surfactant is a nonionic surfactant. In some embodiments, the de-emulsifying surfactant is a secondary ether polyol. In some embodiments, the de-emulsifying surfactant is TERGITOL L-62 (Dow Chemical Company). In some embodiments, the amount of de-emulsifying surfactant is sufficient to remove emulsions from the fermentation broth or microbial biomass, or both. In certain embodiments, the microbial biomass is de-emulsified with 0.1-2.0% de-emulsifying surfactant. In certain embodiments, the microbial biomass is de-emulsified with 0.2-1.0% de-emulsifying surfactant. In certain embodiments, the microbial biomass is de-emulsified with 0.3-1.0% de-emulsifying surfactant. In certain embodiments, the microbial biomass is de-emulsified with 0.25-0.75% de-emulsifying surfactant. In certain embodiments, the microbial biomass is de-emulsified with about 0.6% de-emulsifying surfactant. In certain embodiments, the microbial biomass is de-emulsified with 0.6±0.1% de-emulsifying surfactant. In certain embodiments, the microbial biomass is de-emulsified with 0.6% de-emulsifying surfactant.

In certain embodiments, the methods comprise the steps of acidifying and disrupting the microbial biomass, heating the resulting composition, contacting the resulting composition with a surfactant capable of releasing the one or more water-immiscible compounds from the microbial biomass, and recovering the one or more water-immiscible compounds.

The microbial biomass can be obtained by any technique deemed suitable by the person of skill. In typical embodiments, the microbial biomass is obtained from a fermentation medium. Exemplary fermentation techniques are described in a section below. In particular embodiments, cells producing one or more water-immiscible compound are cultured in a fermentation medium. In certain embodiments, the aqueous medium is separated from microbial biomass by, for example, centrifugation or filtration. A portion of the one or more water-immiscible compounds can emulsify with the aqueous fermentation medium. Another portion of the one or more water-immiscible compounds can remain with the microbial biomass. The methods and compositions provided herein are capable of recovering one or more water-immiscible compounds from this portion. The microbial biomass typically comprises cells and cellular debris. In certain embodiments, the microbial biomass further comprises fermentation medium.

In the methods, the microbial biomass is treated by acidifying and disrupting. These steps can be carried out in any order, or they can be combined. In certain embodiments, the microbial biomass is acidified then disrupted. In certain embodiments, the microbial biomass is disrupted then acidified. In certain embodiments, the microbial biomass is acidified and disrupted simultaneously. Simultaneous acidification and disruption can be achieved when each step overlaps in time with the other.

The microbial biomass can be acidified by any technique apparent to those of skill in the art. In certain embodiments, the microbial biomass is acidified to a pH of 1-4. In certain embodiments, the microbial biomass is acidified to a pH of 1.5-4. In certain embodiments, the microbial biomass is acidified to a pH of 2-4. In certain embodiments, the microbial biomass is acidified to a pH of 2-3.5. In certain embodiments, the microbial biomass is acidified to a pH of 2-3. In certain embodiments, the microbial biomass is acidified to a pH of about 2.5. In certain embodiments, the microbial biomass is acidified to a pH of $2.5\pm0.2$. In certain embodiments, the microbial biomass is acidified to a pH of $2.5\pm0.1$. In certain embodiments, the microbial biomass is acidified to a pH of about 2.5. In certain embodiments, the microbial biomass is acidified to a pH of about 2.5.

The pH can be adjusted with any pH adjusting agent. In certain embodiments, the pH adjusting agent is an inorganic acid. In certain embodiments, the pH adjusting agent is selected from the group consisting of hydrochloric acid, nitric acid, sulfuric acid, and combinations thereof. In certain embodiments, the pH adjusting agent is hydrochloric acid. In certain embodiments, the pH adjusting agent is nitric acid. In certain embodiments, the pH adjusting agent is sulfuric acid.

The microbial biomass can be disputed by any technique apparent to those of skill in the art. Useful techniques include mechanical disruption, sonication, freezing and thawing, grinding, chemical disruption, enzymatic disruption, and combinations thereof. In certain embodiments, the microbial biomass is agitated with glass beads, for instance in a bead mill. In certain embodiments, the microbial biomass is frozen, for instance in liquid nitrogen, and pulverized. In certain embodiments, the microbial biomass is pressed, for instance, with a Hughes press or a French press. In certain embodiments, the microbial biomass is disrupted in a physical cell disruptor under pneumatic or hydraulic pressure. In certain embodiments, the microbial biomass is disrupted by pressure cycling technology. In certain embodiments, the microbial biomass is disrupted with a microfluidizer. In certain embodiments, the microbial biomass is disrupted by ultrasound. In certain embodiments, the microbial biomass is disrupted by thermolysis. In certain embodiments, the microbial biomass is disrupted by decompression. In certain embodiments, the microbial biomass is disrupted by osmotic shock. In certain embodiments, the microbial biomass is disrupted by chemical disruption. Useful chemicals include urea, butanol, and isopentanol. In certain embodiments, the disruption is by enzymatic disruption. Useful enzymes include lysozyme, labiase, achromopeptidase, cellulase, snailase, glucanases, mannanases, and chitnases.

In certain embodiments, the disruption is with a high pressure homogenizer. In certain embodiments, the homogenizer pressure is from 600 bar to 1000 bar. In certain embodiments, the homogenizer pressure is from 700 bar to 1000 bar. In certain embodiments, the homogenizer pressure is from 800 bar to 1000 bar. In certain embodiments, the homogenizer pressure is from 800 bar to 900 bar. In certain embodiments, the homogenizer pressure is at $900\pm50$ bar. In certain embodiments, the homogenizer pressure is at $900\pm25$ bar. In certain embodiments, the homogenizer pressure is at about 900. In certain embodiments, the homogenizer pressure is at 900 bar.

In the methods, the acidified, disrupted microbial biomass is then heated. Heating can be by any technique apparent to the person of skill. In particular embodiments, heat is applied to the microbial biomass. In certain embodiments, the microbial biomass is heated to 55-80° C. In certain embodiments, the microbial biomass is heated to 60-80° C. In certain embodiments, the microbial biomass is heated to 55-75° C. In certain embodiments, the microbial biomass is heated to 65-75° C. In certain embodiments, the microbial biomass is heated to about 70° C. In certain embodiments, the microbial biomass is heated to about $70\pm2.5$° C.

The heated microbial biomass is contacted with a surfactant. The surfactant is a surfactant capable of releasing an amount of the one or more water-immiscible compounds from the microbial biomass. In certain embodiments, the methods release at least 10% of the water-immiscible compound from the microbial biomass. In certain embodiments, the methods release at least 20% of the water-immiscible compound from the microbial biomass. In certain embodiments, the methods release at least 25% of the water-immiscible compound from the microbial biomass. In certain embodiments, the methods release at least 30% of the water-immiscible compound from the microbial biomass. In certain embodiments, the methods release at least 40% of the water-immiscible compound from the microbial biomass. In certain embodiments, the methods release at least 50% of the water-immiscible compound from the microbial biomass. In certain embodiments, the methods release at least 60% of the water-immiscible compound from the microbial biomass. In certain embodiments, the methods release at least 70% of the water-immiscible compound from the microbial biomass. In certain embodiments, the methods release at least 75% of the water-immiscible compound from the microbial biomass.

The surfactant can be any surfactant deemed suitable by the person of skill. In certain embodiments, the surfactant is an ionic surfactant. In certain embodiments, the surfactant is an anionic surfactant. In certain embodiments, the surfactant is a polyanionic surfactant. In certain embodiments, the surfactant is a sulfonated surfactant. In certain embodiments, the surfactant is a sulfonated phenyl ether detergent. In certain embodiments, the surfactant is a disulfonated phenyl ether detergent. In certain embodiments, the surfactant is:

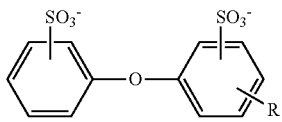

or a salt thereof, wherein R is $C_{6-16}$ alkyl. In certain embodiments, the surfactant is selected from the group consisting of DOWFAX C6L, DOWFAX 3B2, DOWFAX C10L, DOWFAX 2A1, DOWFAX 8390, and DOWFAX 30599. In particular embodiments, the surfactant is according to the formula above, where R is $C_{12}$ alkyl. In particular embodiments, the surfactant is according to the formula above, where R is branched $C_{12}$ alkyl. In certain embodiments, the salt is a sodium salt. In particular embodiments, the surfactant is DOWFAX 2A1.

In certain embodiments, the surfactant has a surface tension of 30-40 dynes/com at 1 wt % actives, 25° C., pH 7 or 12.5. In certain embodiments, the surfactant has a Ross-Miles foam height of 120-160 mm at 1 wt % actives, 25° C., and pH 7, initial time. In certain embodiments, the surfactant has a Ross-Miles foam height of 120-160 mm at 1 wt % actives, 25° C., pH 7, 5 minutes. In certain embodiments, the surfactant has a Ross-Miles foam height of 130-150 mm at 1 wt % actives, 25° C., and pH 12.5, initial time. In certain embodiments, the surfactant has a Ross-Miles foam height of 110-150 mm at 1 wt % actives, 25° C., pH 12.5, 5 minutes.

The surfactant is contacted with the microbial biomass in an amount sufficient to release an amount of the one or more water-immiscible compounds. In certain embodiments, the microbial biomass is contacted with 0.02 to 2.0% surfactant. In certain embodiments, the microbial biomass is contacted with 0.05 to 2.0% surfactant. In certain embodiments, the microbial biomass is contacted with 0.1 to 2.0% surfactant. In certain embodiments, the microbial biomass is contacted with 0.2 to 2.0% surfactant. In certain embodiments, the microbial biomass is contacted with 0.2 to 1.8% surfactant. In certain embodiments, the microbial biomass is contacted with 0.2 to 1.7% surfactant. In certain embodiments, the microbial biomass is contacted with 0.2 to 1.6% surfactant. In certain embodiments, the microbial biomass is contacted with 0.2 to 1.5% surfactant. In certain embodiments, the microbial biomass is contacted with 0.2 to 1.4% surfactant. In certain embodiments, the microbial biomass is contacted with 0.2 to 1.3% surfactant. In certain embodiments, the microbial biomass is contacted with 0.2 to 1.2% surfactant. In certain embodiments, the microbial biomass is contacted with 0.4 to 1.2% surfactant. In certain embodiments, the microbial biomass is contacted with 0.6 to 1.2% surfactant. In certain embodiments, the microbial biomass is contacted with 0.8 to 1.2% surfactant. In certain embodiments, the microbial biomass is contacted with about 1.0% surfactant. In certain embodiments, the microbial biomass is contacted with 1.0±0.1% surfactant.

Once the one or more water-immiscible compounds are released from the microbial biomass, it may be recovered or isolated for subsequent use using any suitable separation and purification method known in the art. In some embodiments, an organic phase comprising the one or more water-immiscible compounds is separated from the fermentation by centrifugation. In other embodiments, an organic phase comprising one or more water-immiscible compounds separates from the fermentation spontaneously. In other embodiments, an organic phase comprising the one or more water-immiscible compounds is separated from the fermentation by adding a de-emulsifier and/or a nucleating agent into the fermentation reaction. Illustrative examples of de-emulsifiers include flocculants and coagulants. Illustrative examples of nucleating agents include droplets of the water-immiscible compound itself and organic solvents such as dodecane, isopropyl myristate, and methyl oleate.

In some embodiments, the one or more water-immiscible compounds are separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In certain embodiments, the methods recover at least 10% of the water-immiscible compound from the microbial biomass. In certain embodiments, the methods recover at least 20% of the water-immiscible compound from the microbial biomass. In certain embodiments, the methods recover at least 25% of the water-immiscible compound from the microbial biomass. In certain embodiments, the methods recover at least 30% of the water-immiscible compound from the microbial biomass. In certain embodiments, the methods recover at least 40% of the water-immiscible compound from the microbial biomass. In certain embodiments, the methods recover at least 50% of the water-immiscible compound from the microbial biomass. In certain embodiments, the methods recover at least 60% of the water-immiscible compound from the microbial biomass. In certain embodiments, the methods recover at least 70% of the water-immiscible compound from the microbial biomass. In certain embodiments, the methods recover at least 75% of the water-immiscible compound from the microbial biomass.

In some embodiments, at least one water-immiscible compound is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of a water-immiscible compounds refers to a water-immiscible compound that is free from other water-immiscible compounds and/or contaminants.

In certain embodiments, provided herein are methods for recovering a water-immiscible compound from a microbial biomass comprising the steps of acidifying the microbial biomass to about pH 2.5, and then disrupting the microbial biomass in a homgenizer at about 900 bar, to form an acidified, disrupted microbial biomass; heating the acidified, disrupted microbial biomass at about 70° C. to form a heated, acidified, disrupted microbial biomass; contacting the heated, acidified, disrupted microbial biomass with about 1% DOWFAX 2A1 to release the one or more water immiscible compounds from the microbial biomass; and recovering the one or more water immiscible compounds.

In certain embodiments, provided herein are methods for recovering a water-immiscible compound from a microbial biomass comprising the steps of disrupting the microbial biomass in a homgenizer at about 900 bar, and then acidifying the microbial biomass to about pH 2.5, to form an acidified, disrupted microbial biomass; heating the acidified, disrupted microbial biomass at about 70° C. to form a heated, acidified, disrupted microbial biomass; contacting the heated, acidified, disrupted microbial biomass with about 1% DOWFAX 2A1 to release the one or more water immiscible compounds from the microbial biomass; and recovering the one or more water immiscible compounds.

In certain embodiments, the total amount of surfactant consumed is increased compared to a comparable method that lacks one or more of the steps provided herein. In certain embodiments, addition of the second surfactant (e.g. DOWFAX 2A1) increases total surfactant consumption. In certain embodiments, total surfactant consumption is increased by at least 5%. In certain embodiments, total surfactant consumption is increased by 5-10%. In certain embodiments, total surfactant consumption is increased by about 7%.

Host Cells, Cell Culture, and Fermentation

The microbial biomass may be obtained by any fermentation technique apparent to the person of skill. In certain embodiments, a population of one or more host cells is grown in a culture medium comprising a carbon source. In certain embodiments, the culturing step is for a period of at least about 12, 24, 36, 48, 60, 72, 84, 96 or more than 96 hours. In certain embodiments, the culturing step is for a period of time sufficient for the population to reach a cell density ($OD_{600}$) of between about 0.01 and 400. In certain embodiments, the population or the subpopulation of host cells is cultured for a period of about 3 to 20 days.

The host cells can be any host cells deemed suitable to the person of skill. In certain embodiments, the host cells are naturally occurring. In particular embodiments, the host cells are genetically modified. In certain embodiments, the host cells are modified to produce a water-immiscible compound. In certain embodiments, the water-immiscible compound is selected from the group consisting of an isoprenoid, a polyketide, and a fatty acid, or a combination thereof.

In some embodiments, the method provided herein is sufficient for producing one or more water-immiscible compounds in an amount greater than about 1, 5, 10, 25, 50, or 100 grams per kg of fermentation broth. In some embodiments, the recombinantly produced water-immiscible compound is produced in an amount from about 1 to 250 grams, about 1 to 200 grams, about 1 to 150 grams, about 1 to 100 grams, about 50 to 250 grams, about 50 to 200 grams, about 50 to 150 grams, more than about 100 grams, or more than about 150 grams, per kilogram broth. In some embodiments, the recombinantly produced water-immiscible compound is produced in an amount of about 160 grams per kilogram broth.

In some embodiments, the method provided herein is sufficient for producing one or more water-immiscible compounds in an amount greater than about 3 grams per gram of dry cell weight. In some embodiments, the recombinantly produced water-immiscible compound is produced in an amount from about 0.01 to about 10 grams, about 0.1 to about 10 grams, about 0.5 to about 5 grams, about 1 to about 5 grams, more than about 0.2 gram, more than about 0.3 gram, more than about 0.4 gram, more than about 0.5 gram, more than about 1 gram, more than about 2 grams, or more than about 3 grams, per gram of dry cell weight.

In certain embodiments, the microbial biomass comprises one or more genetically modified host cells. In certain embodiments, genetically modified host cells are microorganisms (e.g., a genetically modified *Saccharomyces cerevisiae* cell) comprising heterologous nucleic acids.

The genetically modified host cells according to certain embodiments may be modified to produce heterologous water-immiscible compounds (e.g., acetyl Co-A derived compound). For example, the genetically modified host cells may further comprise heterologous nucleotide sequences encoding one or more enzymes of a biosynthetic pathway for producing water-immiscible compounds. In these embodiments, the genetically modified host cells produce greater amounts of one or more compounds biosynthesized from acetyl-CoA compared to a parent host cell lacking the genetic modifications described herein.

In certain embodiments, provided herein are genetically modified host cells that comprise a stabilization construct for stabilized production of heterologous water-immiscible compounds. In certain embodiments, the genetically modified host cells provided herein comprise one or more heterologous nucleic acids encoding one or more enzymes of a biosynthetic pathway for producing a heterologous water-immiscible compound, and one or more heterologous nucleic acids encoding one or more cell-growth-affecting proteins, wherein each of the heterologous nucleic acids is operably linked to a commonly regulated promoter.

In certain embodiments, various combinations and sub-combinations of nucleic acids and constructs described herein may be introduced into genetically modified host cells to stabilize expression of heterologous nucleic acids encoding biosynthetic enzymes for production of water-immiscible compounds. For example, heterologous water-immiscible compound producing host cells can be further modified to comprise a stabilization construct and a fusion protein described herein.

The heterologous nucleic acids described herein may be introduced into host cells using any suitable vectors described herein or those known in the art. Methods for genetically modifying host cells using expression vectors or chromosomal integration constructs, e.g., to effect increased production of one or more water-immiscible compounds in a host cell, are well known in the art. See, for example, Sherman, F., et al., *Methods Yeast Genetics*, Cold Spring Harbor Laboratory, N.Y. (1978); Guthrie, C., et al. (Eds.) *Guide To Yeast Genetics and Molecular Biology* Vol. 194, Academic Press, San Diego (1991); Sambrook et al., 2001, *Molecular Cloning—A Laboratory Manual*, $3^{rd}$ edition, Cold Spring Harbor Laboratory, Cold Spring Harbor, N.Y.; and Ausubel et al., eds., Current Edition, *Current Protocols in Molecular Biology*, Greene Publishing Associates and Wiley Interscience, NY.; the disclosures of which are incorporated herein by reference. In addition, inhibition of gene expression, e.g., which results in increased production of one or more water-immiscible compounds in the cell, may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

In some embodiments, increased production of water-immiscible compound in the cell is effected by the use of expression vectors to express a particular protein, e.g., a protein involved in a biosynthetic pathway as described above. Generally, expression vectors are recombinant polynucleotide molecules comprising replication signals and expression control sequences, e.g., promoters and terminators, operably linked to a nucleotide sequence encoding a polypeptide. Expression vectors useful for expressing polypeptide-encoding nucleotide sequences include viral vectors (e.g., retroviruses, adenoviruses and adeno-associated viruses), plasmid vectors, and cosmids. Illustrative examples of expression vectors suitable for use in yeast cells include, but are not limited to CEN/ARS and 2μ, plasmids. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

Expression vectors and chromosomal integration constructs can be introduced into host cells by any method known to one of skill in the art without limitation. See, for example, Hinnen et al., *Proc. Natl. Acad. Sci. USA* 75:1292-3 (1978); Cregg et al., *Mol. Cell. Biol.* 5:3376-3385 (1985); U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Exemplary techniques include, but are not limited to, spheroplasting, electroporation, PEG 1000 mediated transformation, and lithium acetate or lithium chloride mediated transformation.

Cells useful in the methods and compositions provided herein include any cell capable of producing fusion proteins. In some embodiments, cells are capable of naturally or recombinantly producing a water-immiscible compound, e.g., an isoprenoid, a polyketide, a fatty acid, and the like. In some embodiments, the cell is a prokaryotic cell. In some embodiments, the cell is a bacterial cell. In some embodiments, the cell is an *Escherichia coli* cell. In some embodiments, the cell is a eukaryotic cell. In some embodiments, the cell is a yeast cell. In some embodiments, the cell is a *Saccharomyces cerevisiae* cell. In some embodiments, the cell is a mammalian cell. In some embodiments, the cell is a Chinese hamster ovary (CHO) cell, a COS-7 cell, a mouse fibroblast cell, a mouse embryonal carcinoma cell, or a mouse embryonic stem cell. In some embodiments, the cell is an insect cell. In some embodiments, the cell is a S2 cell, a Schneider cell, a S12 cell, a 5B1-4 cell, a Tn5 cell, or a Sf9 cell. In some embodiments, the cell is a unicellular eukaryotic organism cell, for example, a microbial cell.

In some embodiments, the cell is a mycelial bacterial cell. In some embodiments, the mycelial bacterial cell is of the class actinomycetes. In particular embodiments, the mycelial bacterial cell is of the genera *Streptomyces*, for example, *Streptomyces ambofaciens, Streptomyces avermitilis, Streptomyces azureus, Streptomyces cinnamonensis, Streptomyces coelicolor, Streptomyces curacoi, Streptomyces erythraeus, Streptomyces fradiae, Streptomyces galilaeus, Streptomyces glaucescens, Streptomyces hygroscopicus, Streptomyces lividans, Streptomyces parvulus, Streptomyces peucetius, Streptomyces rimosus, Streptomyces roseofulvus, Streptomyces thermotolerans, Streptomyces violaceoruber.*

In another embodiment, the cell is a fungal cell. In a more particular embodiment, the cell is a yeast cell. Yeasts useful in the methods and compositions provided herein include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkera, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis*, and *Zygozyma*, among others.

In particular embodiments, useful yeasts in the methods and compositions provided herein include *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus, Arxula adeninivorans*, or *Hansenula polymorpha* (now known as *Pichia angusta*). In some embodiments, the microbe is a strain of the genus *Candida*, such as *Candida lipolytica, Candida guilliermondii, Candida krusei, Candida pseudotropicalis*, or *Candida utilis*.

In a particular embodiment, the cell is a *Saccharomyces cerevisiae* cell. In some embodiments, the strain of the *Saccharomyces cerevisiae* cell is selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the strain of *Saccharomyces cerevisiae* is selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the cell is a haploid microbial cell. In other embodiments, the cell is a diploid microbial cell. In some embodiments, the cell is heterozygous. In other embodiments, the cell is homozygous other than for its mating type allele (i.e., if the cell should sporulate, the resulting four haploid microbial cells would be genetically identical except for their mating type allele, which in two of the haploid cells would be mating type a and in the other two haploid cells would be mating type alpha).

In some embodiments, the cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

Exemplary water-immiscible compound producing cells, e.g., cells recombinantly producing isoprenoids, polyketides, and fatty acids, and methods for generating such cells, are provided below.

In certain embodiments, the genetically modified host cells provided in the present methods are capable of producing a heterologous isoprenoid and comprise at least one heterologous nucleic acid encoding an isoprenoid pathway enzyme selected from the group consisting of: (a) an enzyme that condenses two molecules of acetyl-coenzyme A to form acetoacetyl-CoA; (b) an enzyme that condenses acetoacetyl-CoA with another molecule of acetyl-CoA to form 3-hydroxy-3-methylglutaryl-CoA (HMG-CoA); (c) an enzyme that converts HMG-CoA into mevalonate; (d) an enzyme that converts mevalonate into mevalonate 5-phosphate; (e) an enzyme that converts mevalonate 5-phosphate into mevalonate 5-pyrophosphate; (0 an enzyme that converts mevalonate 5-pyrophosphate into IPP; (g) an enzyme that converts IPP into DMAPP; (h) a polyprenyl synthase that can condense IPP and/or DMAPP molecules to form polyprenyl compounds containing more than five carbons; (i) an enzyme that condenses IPP with DMAPP to form GPP; (j) an enzyme that condenses two molecules of IPP with one molecule of DMAPP; (k) an enzyme that condenses IPP with GPP to form FPP; (1) an enzyme that condenses IPP and DMAPP to form GGPP; and (m) an enzyme that condenses IPP and FPP to form GGPP.

In certain embodiments, the host cells further comprise a heterologous nucleic acid encoding an enzyme that modifies a polyprenyl, selected from the group consisting of a geraniol synthase, a linalool synthase, a limonene synthase, a myrcene synthase, an ocimene synthase, an α-pinene synthase, β-pinene synthase, a sabinene synthase, a γ-terpinene synthase, a terpinolene synthase, an amorphadiene synthase, an α-farnesene synthase, a β-farnesene synthase, a farnesol synthase, a nerolidol synthase, a patchouliol synthase, a nootkatone synthase, and an abietadiene synthase.

In certain embodiments, the host cells comprise a plurality of heterologous nucleic acids encoding all the enzymes of a mevalonate pathway. In some embodiments, the isoprenoid is selected from the group consisting of a hemiterpene, monoterpene, diterpene, triterpene, tetraterpene, and polyterpene. In some embodiments, the isoprenoid is a $C_5$-$C_{20}$ isoprenoid. In some embodiments, the isoprenoid is a sesquiterpene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene.

In certain embodiments, the host cells are capable of producing a polyketide and comprises at least one heterologous nucleic acid encoding a polyketide synthesis enzyme, wherein the polyketide synthesis enzyme is selected from the group consisting of: (a) an enzyme that condenses at least one of acetyl-CoA and malonyl-CoA with an acyl carrier protein; (b) an enzyme that condenses a first reactant selected from the group consisting of acetyl-CoA and malonyl-CoA with a second reactant selected from the group consisting of malonyl-CoA or methylmalonyl-CoA to form a polyketide product; (c) an enzyme that reduces a β-keto chemical group on a polyketide compound to a β-hydroxy group; (d) an enzyme that dehydrates an alkane chemical group in a polyketide compound to produce an α-β-unsaturated alkene; (e) an enzyme that reduces an α-β-double-bond in a polyketide compound to a saturated alkane; and (f) an enzyme that hydrolyzes a polyketide compound from an acyl carrier protein.

In certain embodiments, the polyketide is a lipid having at least one of antibiotic, antifungal, and antitumor activity. In some embodiments, the polyketide is selected from the group consisting of a macrolid, an antibiotic, an antifungal, a cytostatic compound, an anticholesterolemic compound, an antiparasitic compound, a coccidiostatic compound, an animal growth promoter and an insecticide.

In certain embodiments, the host cells are capable of producing a fatty acid and comprises at least one heterologous nucleic acid encoding a fatty acid synthesis enzyme, wherein the fatty acid synthesis enzyme is selected from the group consisting of: (a) an enzyme that covalently links at least one of acetyl-CoA and malonyl-CoA to an acyl carrier protein (ACP); (b) an enzyme that condenses acetyl-ACP and malonyl-ACP to form acetoacetyl-ACP; (c) reduce the double bond in acetoacetyl-ACP with NADPH to form a hydroxyl group in D-3-hydroxybutyryl hydroxylase-ACP; (d) an enzyme that dehydrates D-3-Hydroxybutyryl hydroxylase-ACP to create a double bond between the beta- and gamma-carbons forming crotonyl-ACP; (e) an enzyme that reduces crotonyl ACP with NADPH to form butyryl-ACP; and (f) an enzyme that hydrolyzes a C16 acyl compound from an acyl carrier protein to form palmitate. In some embodiments, the fatty acid is selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In some embodiments, the method provided herein is sufficient for producing one or more water-immiscible compounds in an amount greater than about 10 grams per liter of fermentation medium. In some such embodiments, the water-immiscible compound is produced in an amount from about 10 to about 50 grams, more than about 15 grams, more than about 20 grams, more than about 25 grams, or more than about 30 grams per liter of cell culture.

Isoprenoid Compounds

In some embodiments, the water-immiscible compound is an isoprenoid. Isoprenoids are derived from isopentenyl pyrophosphate (IPP), which can be biosynthesized by enzymes of the mevalonate-dependent ("MEV") pathway or the 1-deoxy-D-xylulose 5-diphosphate ("DXP") pathway.

MEV Pathway

In some embodiments of the methods provided herein, the genetically modified microorganism comprises one or more heterologous nucleotide sequences encoding one or more enzymes of the MEV pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the isoprenoid producing cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the isoprenoid producing cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the isoprenoid producing cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145, complement 712315.713670; *Saccharomyces cerevisiae*).

In some embodiments, the isoprenoid producing cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

In some embodiments, the isoprenoid producing cell comprises one or more heterologous nucleotide sequences encoding more than one enzyme of the MEV pathway. In some embodiments, the isoprenoid producing cell comprises one or more heterologous nucleotide sequences encoding two enzymes of the MEV pathway. In some embodiments, the isoprenoid producing cell comprises one or more heterologous nucleotide sequences encoding an enzyme that can convert HMG-CoA into mevalonate and an enzyme that can convert mevalonate into mevalonate 5-phosphate. In some embodiments, the isoprenoid producing cell comprises one or more heterologous nucleotide sequences encoding three enzymes of the MEV pathway. In some embodiments, the isoprenoid producing cell comprises one or more heterologous nucleotide sequences encoding four enzymes of the MEV pathway. In some embodiments, the isoprenoid producing cell comprises one or more heterologous nucleotide sequences encoding five enzymes of the MEV pathway. In some embodiments, the isoprenoid producing cell comprises one or more heterologous nucleotide sequences encoding six enzymes of the MEV pathway.

Figure 2:
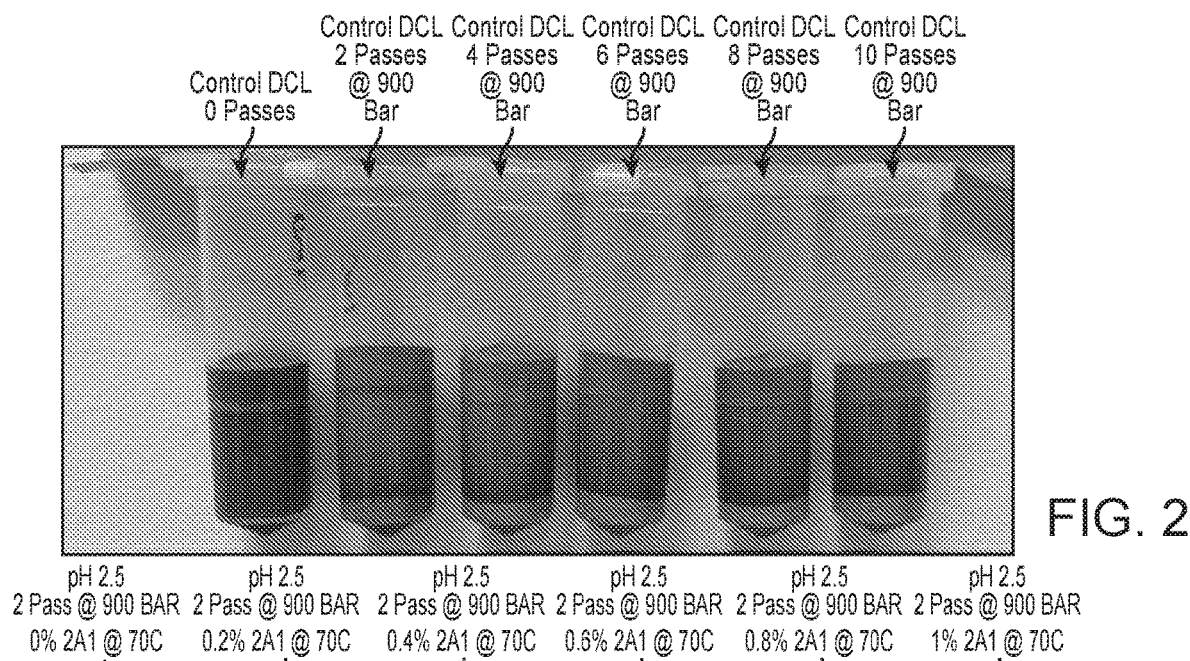
FIG. 2 provides samples from homogenization steps.

In some embodiments, the isoprenoid producing cell further comprises a heterologous nucleotide sequence encoding an enzyme that can convert IPP generated via the MEV pathway into its isomer, dimethylallyl pyrophosphate ("DMAPP"). DMAPP can be condensed and modified through the action of various additional enzymes to form simple and more complex isoprenoids (FIG. 2).

DXP Pathway

In some embodiments of the methods provided herein, the isoprenoid producing cell comprises one or more heterologous nucleotide sequences encoding one or more enzymes of the DXP pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme, e.g., 1-deoxy-D-xylulose-5-phosphate synthase, which can condense pyruvate with D-glyceraldehyde 3-phosphate to make 1-deoxy-D-xylulose-5-phosphate. Illustrative examples of nucleotide sequences encoding such an enzyme include but are not limited to: (AF035440; *Escherichia coli*), (NC_002947, locus tag PP0527; *Pseudomonas putida* KT2440), (CP000026, locus tag SPA2301; *Salmonella enterica* Paratyphi, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa* Temecula1), and (NC_003076, locus tag AT5G11380; *Arabidopsis thaliana*).

In some embodiments, the isoprenoid producing cell comprises a heterologous nucleotide sequence encoding an enzyme, e.g., 1-deoxy-D-xylulose-5-phosphate reductoisomerase, which can convert 1-deoxy-D-xylulose-5-phosphate to 2C-methyl-D-erythritol-4-phosphate. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SC05694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In some embodiments, the isoprenoid producing cell comprises a heterologous nucleotide sequence encoding an enzyme, e.g., 4-diphosphocytidyl-2C-methyl-D-erythritol synthase, which can convert 2C-methyl-D-erythritol-4-phosphate to 4-diphosphocytidyl-2C-methyl-D-erythritol. Illustrative examples of nucleotide sequences include but are not limited to: (AF230736; *Escherichia coli*), (NC_007493, locus tag RSP_2835; *Rhodobacter sphaeroides* 2.4.1), (NC_003071, locus tag AT2G02500; *Arabidopsis thaliana*), and (NC_002947, locus tag PP1614; *Pseudomonas putida* KT2440).

In some embodiments, the isoprenoid producing cell comprises a heterologous nucleotide sequence encoding an enzyme, e.g., 4-diphosphocytidyl-2C-methyl-D-erythritol kinase, which can convert 4-diphosphocytidyl-2C-methyl-D-erythritol to 4-diphosphocytidyl-2C-methyl-D-erythritol-2-phosphate. Illustrative examples of nucleotide sequences include but are not limited to: (AF216300; *Escherichia coli*) and (NC_007493, locus tag RSP_1779; *Rhodobacter sphaeroides* 2.4.1).

In some embodiments, the isoprenoid producing cell comprises a heterologous nucleotide sequence encoding an enzyme, 2C-methyl-D-erythritol 2,4-cyclodiphosphate synthase, which can convert 4-diphosphocytidyl-2C-methyl-D-erythritol-2-phosphate to 2C-methyl-D-erythritol 2,4-cyclodiphosphate. Illustrative examples of nucleotide sequences include but are not limited to: (AF230738; *Escherichia coli*), (NC_007493, locus tag RSP_6071; *Rhodobacter sphaeroides* 2.4.1), and (NC_002947, locus tag PP1618; *Pseudomonas putida* KT2440).

In some embodiments, the isoprenoid producing cell comprises a heterologous nucleotide sequence encoding an enzyme, e.g., 1-hydroxy-2-methyl-2-(E)-butenyl-4-diphosphate synthase, which can convert 2C-methyl-D-erythritol 2,4-cyclodiphosphate to 1-hydroxy-2-methyl-2-(E)-butenyl-4-diphosphate. Illustrative examples of nucleotide sequences include but are not limited to: (AY033515; *Escherichia coli*), (NC_002947, locus tag PP0853; *Pseudomonas putida* KT2440), and (NC_007493, locus tag RSP_2982; *Rhodobacter sphaeroides* 2.4.1).

In some embodiments, the isoprenoid producing cell comprises a heterologous nucleotide sequence encoding an enzyme, e.g., isopentyl/dimethylallyl diphosphate synthase, which can convert 1-hydroxy-2-methyl-2-(E)-butenyl-4-diphosphate into either IPP or its isomer, DMAPP. Illustrative examples of nucleotide sequences include but are not limited to: (AY062212; *Escherichia coli*) and (NC_002947, locus tag PP0606; *Pseudomonas putida* KT2440).

In some embodiments, the isoprenoid producing cell comprises one or more heterologous nucleotide sequences encoding more than one enzyme of the DXP pathway. In some embodiments, the isoprenoid producing cell comprises one or more heterologous nucleotide sequences encoding two enzymes of the DXP pathway. In some embodiments, the isoprenoid producing cell comprises one or more heterologous nucleotide sequences encoding three enzymes of the DXP pathway. In some embodiments, the isoprenoid producing cell comprises one or more heterologous nucleotide sequences encoding four enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding six enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding seven enzymes of the DXP pathway.

In some embodiments, "cross talk" (or interference) between the host cell's own metabolic processes and those processes involved with the production of IPP are minimized or eliminated entirely. For example, cross talk is minimized or eliminated entirely when the host microorganism relies exclusively on the DXP pathway for synthesizing IPP, and a MEV pathway is introduced to provide additional IPP. Such a host organism would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the isoprenoid produced by the cell is a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

In some embodiments, the isoprenoid producing cell further comprises a heterologous nucleotide sequence encoding an enzyme that can convert IPP generated via the MEV pathway into DMAPP, e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

In some embodiments, the isoprenoid producing cell further comprises a heterologous nucleotide sequence encoding a polyprenyl synthase that can condense IPP and/or DMAPP molecules to form polyprenyl compounds containing more than five carbons.

In some embodiments, the isoprenoid producing cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha x piperita*), (AF182827; *Mentha x piperita*), (MPI249453; *Mentha x piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the isoprenoid producing cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *SchizoSaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP 873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisiae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

In some embodiments, the isoprenoid producing cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; Catharanthus *roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; Syntrophus aciditrophicus SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP 721015; *Streptococcus mutans* UA159).

In some embodiments, the isoprenoid producing cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM_463918; *Oryza sativa*), (AP004078, Locus BAD07605; *Oryza sativa*), (XM_463918, Locus XP 463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−) β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include, but are not limited to: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include but are not limited to: (AY693650 from *Ocimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes an α-farnesene synthase. Illustrative examples of suitable nucleotide sequences include, but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include, but are not limited to GenBank accession number AF024615 from *Mentha x piperita* (peppermint; gene Tspa11), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of a suitable nucleotide sequence include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

Culture Media and Conditions

Materials and methods for the maintenance and growth of cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing water-immiscible compounds provided herein may be performed in a suitable culture medium in a suitable container, including but not limited to a cell culture plate, a flask, or a fermenter. Further, the methods can be performed at any scale of fermentation known in the art to support industrial production of microbial products. Any suitable fermenter may be used including a stirred tank fermenter, an airlift fermenter, a bubble fermenter, or any combination thereof. In particular embodiments utilizing *Saccharomyces cerevisiae* as the host cell, strains can be grown in a fermenter as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any volume of fermentation, e.g., from lab scale (e.g., about 10 ml to 20 L) to pilot scale (e.g., about 20 L to 500 L) to industrial scale (e.g., about 500 L to >500,000 L) fermentations.

In some embodiments, the culture medium for use in the methods of producing water-immiscible compounds as provided herein includes any culture medium in which a genetically modified microorganism capable of producing a water-immiscible compound can subsist, i.e., support and maintain growth and viability. In some embodiments, the culture medium, also promotes the biosynthetic pathway necessary to produce the desired water-immiscible compound.

In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol. In some embodiments, sugar cane syrup which includes different combinations of carbon source may be used.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, typically greater than about 2 g/L, and typically greater than about 5 g/L. In addition, the concentration of a carbon source, such as glucose, in the culture medium is generally less than about 100 g/L, typically less than about 50 g/L, and more typically less than about 20 g/L. Sometimes the concentration of carbon source can be greater than 100 g/L during a brief period, for example, when cells are initially added to the fermenter. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Any suitable amount of nitrogen sources may be added to the culture medium. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Any suitable amount of phosphate source may be added to the culture medium.

A suitable culture medium can also include a source of magnesium, preferably in the form of a physiologically acceptable salt, such as magnesium sulfate heptahydrate, although other magnesium sources in concentrations that contribute similar amounts of magnesium can be used. Any suitable amount of magnesium source may be added to the culture medium. Further, in some instances it may be desirable to allow the culture medium to become depleted of a magnesium source during culture.

In some embodiments, the culture medium can also include a biologically acceptable chelating agent, such as the dihydrate of trisodium *citrate*. Any suitable amount of chelating agent may be added to the culture medium.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

In some embodiments, the culture medium can also include a biologically acceptable calcium source, including, but not limited to, calcium chloride. In some embodiments, the culture medium can also include sodium chloride. In some embodiments, the culture medium can also include trace metals. Such trace metals can be added to the culture medium as a stock solution that, for convenience, can be prepared separately from the rest of the culture medium. Any suitable amount of calcium source, sodium chloride, and trace metals may be added to the culture medium.

The culture media can include other vitamins, such as biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture during the production stage of the fermentation. In some embodiments, the culture may be supplemented with relatively high concentrations of such components at the outset, for example, of the production stage, so that growth and/or water-immiscible compound production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of water-immiscible compounds. For example, prior to inoculation of the culture medium with an inoculum, the culture medium can be brought to and maintained at a temperature in the range of from about 20° C. to about 45° C., typically to a temperature in the range of from about 25° C. to about 40° C., and more typically in the range of from about 28° C. to about 34° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, typically from about 3.5 to about 7.0, and more typically from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition may occur at glucose concentrations greater than at about 60 g/L, and can be determined readily by trial. Accordingly, when glucose is used as a carbon source the glucose is preferably fed to the fermenter and maintained below detection limits. Alternatively, the glucose concentration in the culture medium is maintained in the range of from about 1 g/L to about 100 g/L, typically in the range of from about 2 g/L to about 50 g/L, and sometimes in the range of from about 5 g/L to about 20 g/L. Although the carbon source concentration can be maintained within desired levels by addition of, for example, a substantially pure glucose solution, it is acceptable to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

EXAMPLES

As used herein, the symbols and conventions used in these processes, schemes and examples, regardless of whether a particular abbreviation is specifically defined, are consistent with those used in the contemporary scientific literature, for example, the *Journal of the American Chemical Society* or the *Journal of Biological Chemistry*. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr. or hrs. (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); $DMSO-d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

This example demonstrates effective release of a water-immiscible compound from a dead cell layer.

Homogenization efficiency was evaluated against a dead cell layer emulsion. The dead cell layer emulsion was homogenized with a Niro Panda high pressure homogenizer at 900 BAR. 1 mL samples were pulled after each discreet pass, and centrifuged to determine if a pellet formed. After 2 passes at 900 BAR, a pellet was observed indicating the homogenizer is causing debris to pellet. The size of the pellet did not appear to increase significantly after 2 passes. See FIG. 2.

Figure 3:
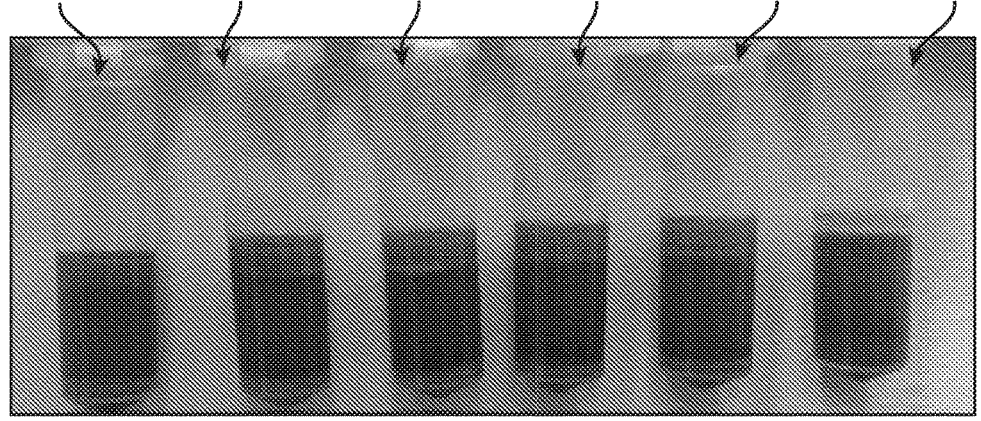
FIG. 3 provides samples from surfactant steps.

The resulting slurry was titrated to pH 2.5 using a 50% nitric acid solution. The anionic detergent, Dowfax 2A1 was added in 0.2% volume/volume increments up to 1% v/v concentration. The aliquots were mixed and centrifuged at 8500 G for 2 minutes. As seen in FIG. 3, at a Dowfax 2A1 concentration of 1%, liberated free oil resides in the top phase while the solids pellet out into the bottom of the centrifuge tube.

Example 2

Four bench-scale recoveries were conducted to determine the recovery yield of crude farnesene oil from the dead cell layer and characterize the different phases in terms of farnesene content and purity.

Figure 4:
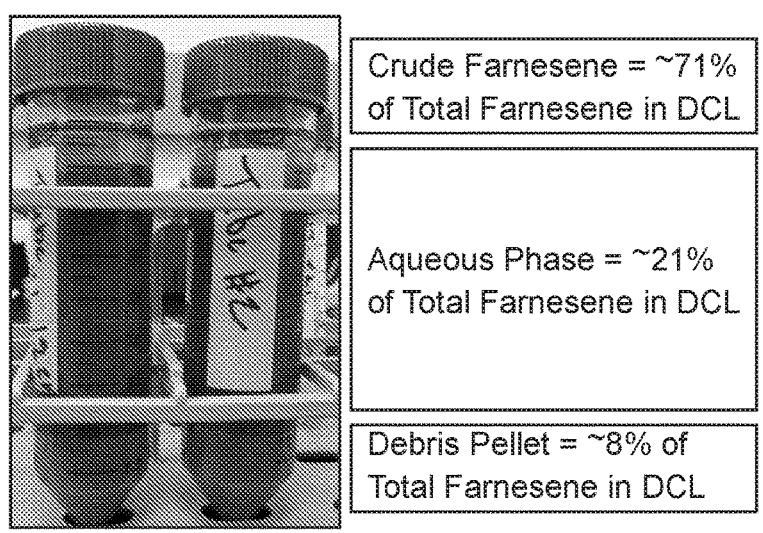
FIG. 4 provides samples following surfactant steps with 71% water-immiscible compound in an organic layer, 21% water-immiscible compound in an aqueous layer, and just 8% water-immiscible compound remaining in a dead cell layer.

For each trial about 100 mL of dead cell layer slurry was titrated to pH 2.5 with 50% nitric acid and homogenized for 2 passes at 900 BAR. DOWFAX 2A1 was added to a 1% v/v concentration and aliquoted into 50 mL centrifuge tubes. The tubes were heated in a 70° C. water bath for approximately 15 min, and centrifuged at 5000×G for 7 min at 70° C. After centrifugation a clear farnesene breakout phase was observed, along with a rag layer phase just beneath, an aqueous phase and a debris pellet on the bottom. See FIG. 4.

The clear, crude, and aqueous phases were discreetly sampled by syringe for farnesene titer. The debris pellet was isolated by decantation, weighed and sampled directly for farnesene titer by gas chromatography analysis. The gas chromatography data are tabulated below.

| Trial | Sample | Volume (mL) | Fene Titer (mg/mL) | Total Fene (mg) | % Fraction |
|---|---|---|---|---|---|
| #1 | DCL Slurry | 45 | 84.66 | 3809.92 | 100% |
| | Pellet | 8 | 38.48 | 307.84 | 8% |
| | Aqueous | 32 | 20.31 | 649.92 | 17% |
| | Crude | 5 | Calculated | 2852.16 | 75% |

-continued

| Trial | Sample | Volume (mL) | Fene Titer (mg/mL) | Total Fene (mg) | % Fraction |
|---|---|---|---|---|---|
| #2 | DCL Slurry | 45 | 84.66 | 3809.7 | 100% |
| | Pellet | 8 | 34.2 | 273.6 | 7% |
| | Aqueous | 32 | 20.71 | 662.72 | 17% |
| | Crude | 5 | Calculated | 2873.38 | 75% |
| #3 | DCL Slurry | 44.28 | 74.27 | 3288.66 | 100% |
| | Pellet | 9.72 | 30.42 | 295.701 | 9% |
| | Aqueous | 31.4 | 23.80 | 747.388 | 23% |
| | Crude | 3.16 | Calculated | 2245.57 | 68% |
| #4 | DCL Slurry | 45.34 | 74.27 | 3367.39 | 100% |
| | Pellet | 9.88 | 31.56 | 311.781 | 9% |

-continued

| Trial | Sample | Volume (mL) | Fene Titer (mg/mL) | Total Fene (mg) | % Fraction |
|---|---|---|---|---|---|
| | Aqueous | 32.38 | 27.26 | 882.834 | 26% |
| | Crude | 3.08 | Calculated | 2172.77 | 65% |
| | Average % Recovery of Crude | | | | 71% |
| | Average % Loss to Aqueous Phase | | | | 21% |
| | Average Loss to Debris Pellet | | | | 8% |

The recovery yields for each step of the four experiments are shown in the Table below.

| Feed description | Trial #1 | Trial #2 | Trial #3 | Trial #4 |
|---|---|---|---|---|
| DCL Slurry Concentration Yield | 63% | 48% | 71% | 64% |
| Homgenization DCL Clarification Yield | 95% | 88% | 74% | 81% |
| Crude Fene Yield | 41% | 48% | 79% | 83% |
| Integrated Yield | 24% | 20% | 41% | 43% |

On average approximately 71% crude farnesene breakout was observed after chemical treatment of the homogenized dead cell layer. Purity analysis of the crude farnesene sampled from the trials are tabulated below.

| Stream | Mass, g | Temp, C | Farnesene Purity wt. % | Farnesene, g |
|---|---|---|---|---|
| 1-Feed | 100.5 | ambient | 7.9% | 7.93 |
| 2-50% Nitric | 2.26 | ambient | 0% | 0 |
| 3-2A1 Detergent | 1.1 | ambient | 0% | 0 |
| 4-Centrifuge Feed | 97.61 | 70 | — | 0 |
| 5-Crude Farnesene | 6.775 | 70 | 92.5% | 6.27 |
| 6-Waste | 90.835 | 70 | 1.4% | 1.24 |

As demonstrated in this example, it is possible to break the dead cell layer emulsion and recover a water-immiscible compound by applying a combination of cell disruption, low pH, and surfactant addition followed by centrifugation.

Example 3

A larger volume of crude farnesene was generated using a conventional process and subsequently distilled using farnesene evaporation conditions (<1 torr, 120° C.). The distilled farnesene was assayed for purity and it was found to satisfy existing specifications. The results are shown in the table below.

| Sample ID | Unit | Nenter Specification | Non-Nenter Specification | Distilled Farnesene from H6395 | Distilled Farnesene from H6466 |
|---|---|---|---|---|---|
| Farnesene | GC wt. % | >95 | >97.2 or >97.4 | 97.85 | 97.99 |
| Water | ppm | <400 | <150 | 121.5 | 75.9 |
| TAN | mg KOH/g | <0.15 | <0.15 | 0.056 | 0.0515 |
| Color | APHA# | Report | <35 | 6 | 10.3 |
| Thermal Dimers | GC Area % | N/A | <0.4 | 0 | 0 |
| Farnesol | GC Area % | N/A | 0.6-1.1 | 0.67 | 0.76 |
| Polymer | GPC Area % | N/A | <0.5 | 0 | 0.01 |
| Bisabolene | GC Area % | N/A | <1 | 0.27 | 0.27 |
| Zingiberene | GC Area % | N/A | <1 | 0.28 | 0.34 |

Example 4

This example demonstrates recovery of a water-immiscible compound from a 300 L fermenter run.

Figure 1B:
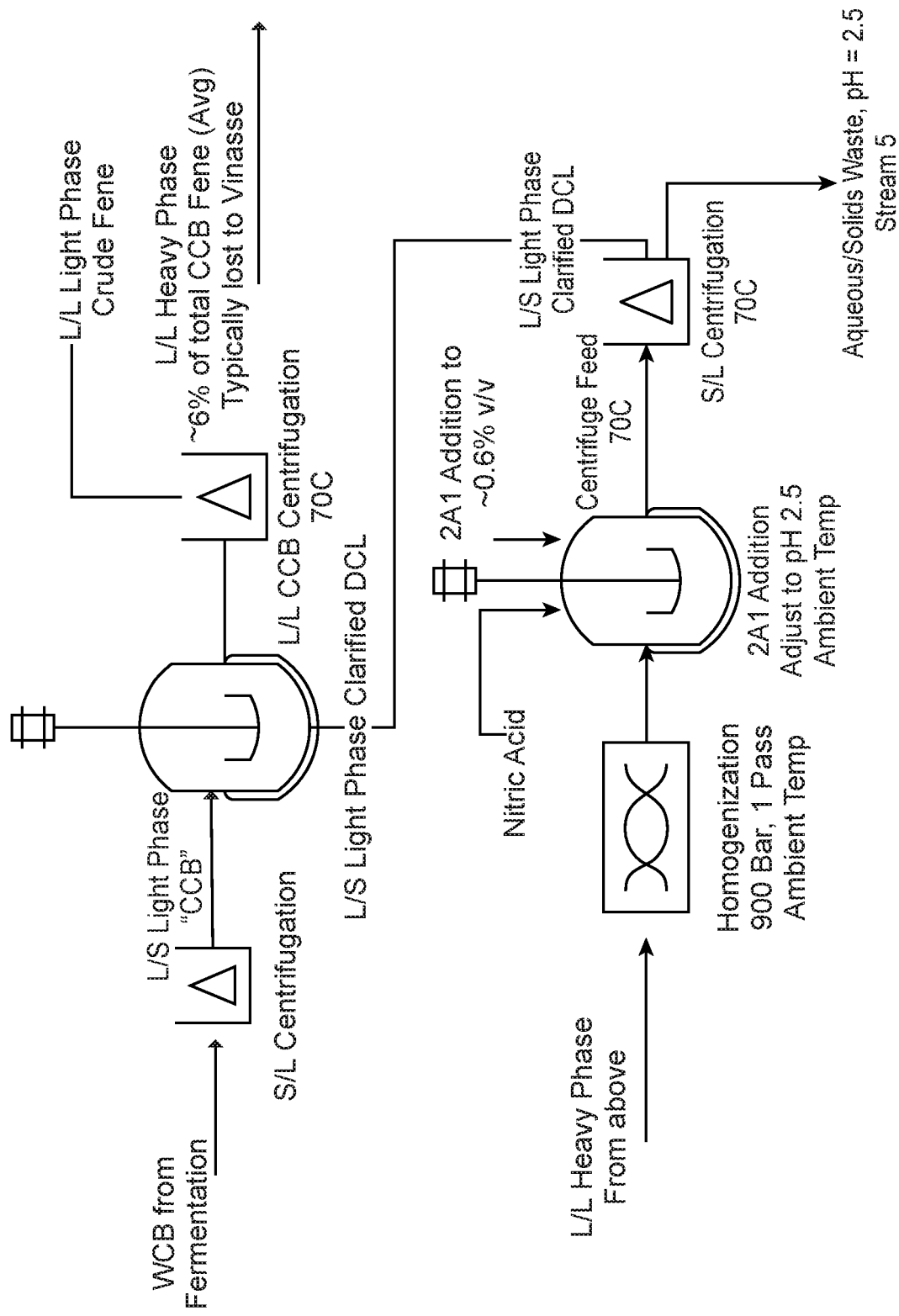
FIG. 1B provides a schematic of a manufacturing scale system for carrying out certain methods provided herein.
Figure 1C:
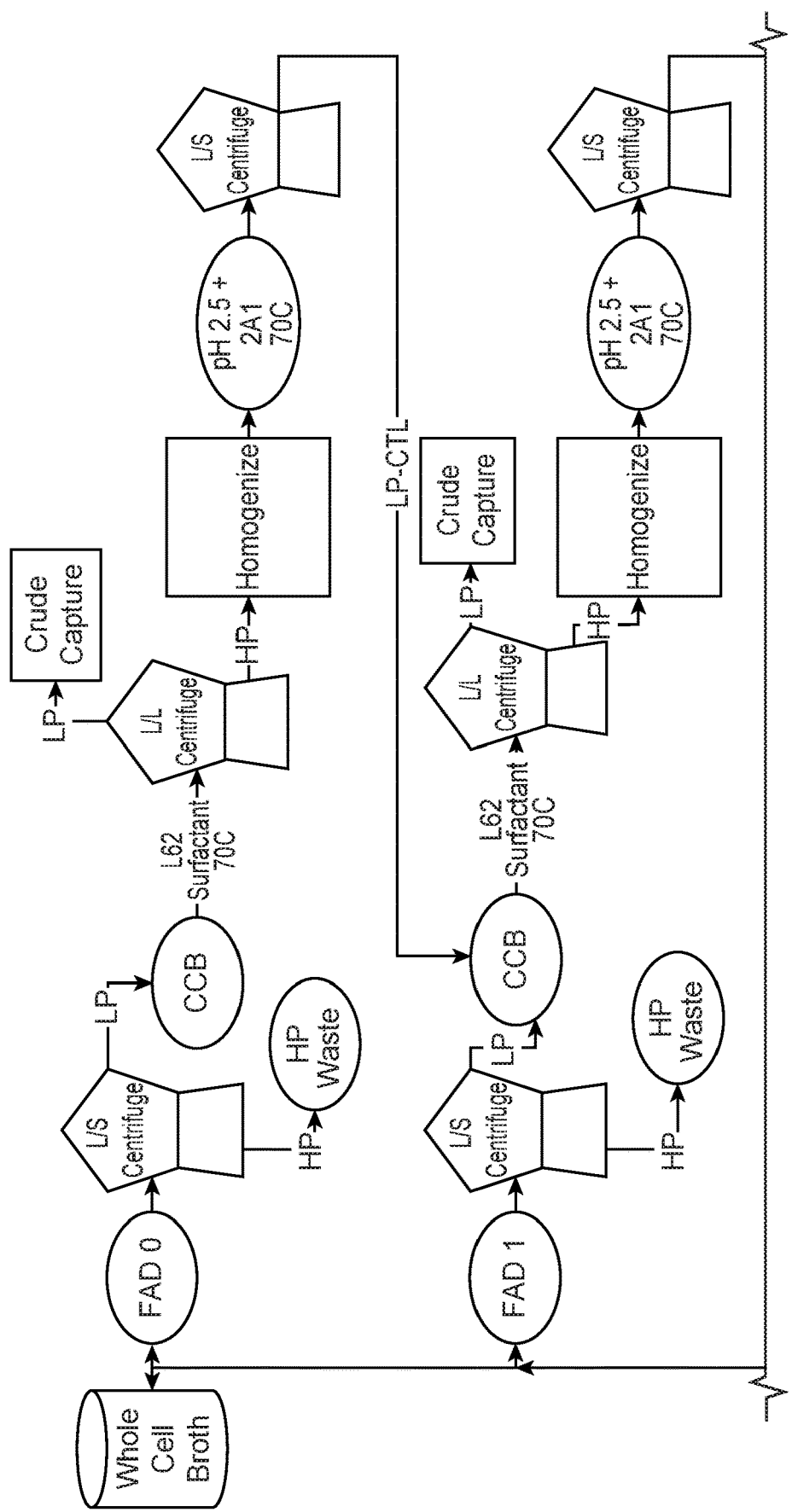
FIG. 1C provides a schematic of a pilot scale system for carrying out certain methods provided herein.
Figure 1C:
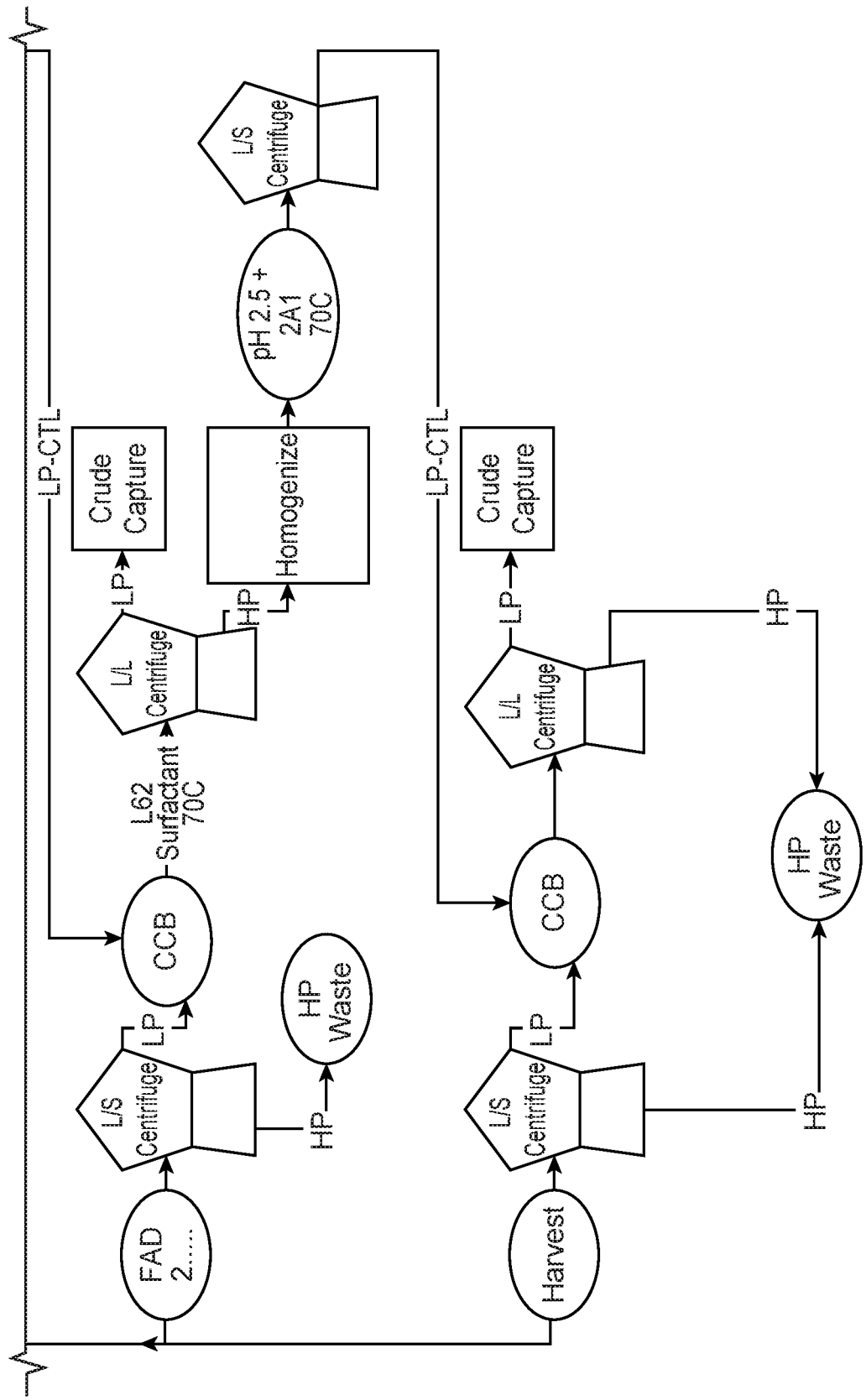

Cells producing farnesene were cultured in a 300 L fermenter. The entire volume of the liquid-liquid heavy phase was run through a NIRO NS3006 L Panther homogenizer for 1 pass at 900 BAR pressure. The lysate is acidified to pH 2.5 with nitric acid and a surfactant (DOWFAX 2A1) is added to a concentration of 0.6%. The treated lysate was heated to 70° C. The dead cell layer solids dropped out and released trapped farnesene recoverable by liquid-liquid centrifugation. A clarification centrifugation was performed on the treated and heated lysate in order to clarify out the dead cell layer solids and concentrate the released farnesene. The recovered light phase ("Clarified Treated Lysate" or "CTL") was added back to the Clarified Concentrated Broth ("CCB") recovered in a subsequent draw. In this manner, the processed liquid-liquid heavy phase and associated losses were added back into the main farnesene recovery process. A schematic of the manufacturing scale and pilot scale processes are shown in FIGS. 1B and 1C.

In a pilot scale system, a farnesene-producing strain was fermented using cane syrup feed for 162 hours. This allowed 2 draws and one harvest (FAD 0, FAD 1, and FAD 2). The CCB was processed with 0.6% Tergitol L-62 surfactant at 70° C. through to crude for the first draw (FAD 0). The entire volume of liquid-liquid heavy phase was homogenized for 1 pass at 900 Bar, and it was then titrated to pH 2.5 using nitric acid. The resulting composition was then mixed with DOWFAX 2A1 surfactant at 0.6% v/v concentration. The treated lysate was heated to 70° C. and centrifuged using the DX-203 to remove dead cell layer solids. This is the CTL stream.

The CCB recovered in the next draw (FAD 1) was split into 2 equal aliquots. The resulting CTL from FAD 0 was added back to one of the aliquots of CCB from FAD1 and run through the liquid-liquid step with 0.6% L-62 surfactant. The second aliquot was processed as the control liquid-liquid stream. The liquid-liquid heavy phase from the CTL-enriched condition was again processed as described above with the resulting CTL added back to a CCB aliquot split from FAD 2. This was the last draw in this fermentation run.

Overall, 4% more crude farnesene was captured compared to the control by processing and recycling the liquid-liquid heavy phase back in to the CCB. Interestingly, addition of the CTL back into the CCB reduced the L-62 requirement to break the emulsion by greater than an order of magnitude; however, when considering the addition of 0.6% 2A1 to the process, the overall surfactant consumption (L-62+2A1) increased by 7%.

The recovery yields from the three liquid-solid separations (FAD 0, 1, 2) are presented in the table below.

| FAD | L/S Recovery Yield |
|---|---|
| FAD 0 | 97.30% |
| FAD 1 | 95.50% |
| FAD 2 | 96.80% |

The CCB from FAD 1 and FAD 2 were split into 2 equal aliquots. One aliquot was enriched with the CTL recovered from the previous FAD and the other aliquot was processed as the control. Both liquid-liquid unit operations were run with the same centrifuge configuration and flow rates in order to minimize equipment performance variability. The liquid-liquid recovery yield for the first draw, FAD 0, was 75% by gain, when measured by the amount of crude recovered from the CCB. The recovery yield measured by loss was 82% when only considering the farnesene losses subtracted from the feed concentration.

| Condition | FAD | % Recovery of Farnesene in Crude | Farnesene Recovered from L/L HP (%) | L/L Recovery by Loss (HP + Disch) w/o CTL (%) | L/L Recovery by loss w/ CTL (%) |
|---|---|---|---|---|---|
| L/L Enriched | FAD 0 | 78% | 75% | 82% | 95% |
| | FAD 1 | 96% | 71% | 95% | 98% |
| | FAD 2 | 98% | 0% | 94% | 99.7% |
| | Avg | 91% | 48% | 90% | 98% |
| L/L Control | FAD 0 | 78% | | 82% | |
| | FAD 1 | 97% | | 95% | |
| | FAD 2 | 95% | | 95% | |
| | Avg | 90% | | 91% | |

| Condition | L/S Recovery Yield | L/L Recovery Yield | Mass of Crude Recovered (kg) | Total Recovery Yield | CTL Recovery Yield | Potential Increase in L/L Recovery | Increase in Crude Vol Recovered |
|---|---|---|---|---|---|---|---|
| Control FAD 0 | 97.30% | 93.20% | 5.15 | 90.7% | 75% | 5% | |
| Control FAD 1 | 95.50% | 95.0% | 13.21 | 90.7% | | | |
| Enriched FAD 1 | 95.50% | 95.2% | 13.91 | 90.9% | 71% | 3% | +5.3% |
| Control FAD 2 | 96.80% | 94.40% | 20.02 | 91.4% | | | |
| Enriched FAD 2 | 96.80% | 93.30% | 20.53 | 90.3% | | | +2.5% |

After addition of the CTL to the CCB, the L-62 requirement to break the CCB emulsion was reduced by an order of magnitude. With the enriched CCB, 34.44 kg of crude water-immiscible compound was recovered, compared to 33.23 kg of crude in the control. This is about a 4% increase in crude volume. The mass of CCB processed was slightly lower in the enriched system yielding a slightly higher Crude/CCB ratio; 22.5% vs 21.6%. There was a about 7% increase in total surfactant consumption (L-62 and 2A1) in the enriched system.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed is:

1. A method for recovering one or more water immiscible compounds from a microbial biomass, comprising the steps of:
    a. treating the microbial biomass by:
        i. acidifying the microbial biomass at a pH of 2-4; and
        ii. disrupting the microbial biomass;
        to form an acidified, disrupted microbial biomass;
    b. heating the acidified, disrupted microbial biomass to form a heated, acidified, disrupted microbial biomass;
    c. contacting the heated, acidified, disrupted microbial biomass with a disulfonated surfactant in an amount sufficient to release at least 30% of the one or more water immiscible compounds from the microbial biomass;
    d. recovering the one or more water immiscible compounds, wherein the water immiscible compounds comprise an isoprenoid, a polyketide, or a fatty acid.

2. The method of claim 1, wherein the acidifying step precedes the disrupting step.

3. The method of claim 1, wherein the disrupting step precedes the acidifying step.

4. The method of claim 1, wherein the disrupting step and the acidifying step are simultaneous.

5. The method of claim 1, wherein the acidifying step is at a pH of 2.5.

6. The method of claim 1, wherein the disrupting step comprises mechanical disrupting, sonicating, freezing/thawing, grinding, chemical disrupting, enzymatic disrupting, or a combination thereof.

7. The method of claim 1, wherein the disrupting step comprises homogenizing with one or more passes through a homogenizer at 600 bar to 1000 bar.

8. The method of claim 1, wherein the disrupting step comprises homogenizing with one or more passes through a homogenizer at about 900 bar.

9. The method of any of claim 1, wherein the heating step is at 60°-80° C.

10. The method of claim 1, wherein the heating step is 70° C.

11. The method of claim 1, wherein the disulfonated surfactant is a disulfonated phenyl ether detergent.

12. The method of claim 1, wherein the disulfonated surfactant comprises:

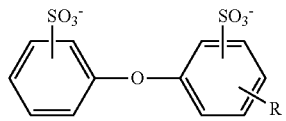

or a salt thereof, wherein R is a $C_6$-$C_{16}$ alkyl.

13. The method of claim 12, wherein R is a $C_{12}$ alkyl.

14. The method of claim 1, wherein the disulfonated surfactant is disodium lauryl phenyl ether disulfonate (DOWFAX 2A1™).

15. The method of claim 1, wherein the heated, acidified, disrupted microbial biomass is contacted with 0.2 to 1.5% disulfonated surfactant.

16. The method of claim 1, wherein the heated, acidified, disrupted microbial biomass is contacted with 1.0% disulfonated surfactant.

17. The method of claim 1, wherein the recovering step comprises centrifugation, solvent extraction, chromatography, or a combination thereof.

18. The method of claim 1, wherein at least 40, 50, 60, 70, or 75% of the one or more water immiscible compounds from the microbial biomass is released.

19. The method of claim 1, comprising the steps of:
 a. treating the microbial biomass by:
  i. acidifying the microbial biomass to a pH of 2.5; and then
  ii. disrupting the microbial biomass in a homogenizer at 900 bar; to form an acidified, disrupted microbial biomass;
 b. heating the acidified, disrupted microbial biomass at 70° C. to form a heated, acidified, disrupted microbial biomass;
 c. contacting the heated, acidified, disrupted microbial biomass with 1% DOWFAX2A1™ to release the one or more water immiscible compounds from the microbial biomass; and
 d. recovering the one or more water immiscible compounds.

20. The method of claim 1, comprising the steps of:
 a. treating the microbial biomass by:
  i. disrupting the microbial biomass in a homogenizer at 900 bar; and then
  ii. acidifying the microbial biomass to a pH of 2.5; to form an acidified, disrupted microbial biomass;
 b. heating the acidified, disrupted microbial biomass at 70° C. to form a heated, acidified, disrupted microbial biomass;
 c. contacting the heated, acidified, disrupted microbial biomass with 1% DOWFAX2A1™ to release the one or more water immiscible compounds from the microbial biomass; and
 d. recovering the one or more water immiscible compounds.

21. The method of claim 1, wherein the microbial biomass has been de-emulsified with a de-emulsifying surfactant prior to step a.

22. The method of claim 21, wherein the de-emulsifying surfactant is TERGITOL L-62™.

23. The method of claim 22, wherein the amount of surfactant consumed is increased compared to the amount used in a comparable method lacking at least step c.

24. The method of claim 1, wherein the microbial biomass is a recombinant yeast.

25. The method of claim 1, wherein the microbial biomass is a recombinant *Saccharomyces cerevisiae*.

26. The method of claim 1, wherein the microbial biomass comprises microbial cells that recombinantly express enzymes producing one or more water immiscible compounds.

27. The method of claim 1, wherein the water immiscible compound is a $C_5$ to $C_{40}$ terpene, $C_5$ to $C_{20}$ terpene, or $C_{15}$ terpene.

28. The method of claim 1, wherein the water immiscible compound is abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene, and valencene.

29. The method of claim 1, wherein the water-immiscible compounds is α-farnesene or β-farnesene.

* * * * *